US012324906B2

(12) United States Patent
Baumbach et al.

(10) Patent No.: US 12,324,906 B2
(45) Date of Patent: Jun. 10, 2025

(54) SYSTEMS AND METHODS FOR DETERMINING A TOTAL BLOOD VOLUME FLOW IN A CARDIAC SUPPORT SYSTEM AND VASCULAR SUPPORT SYSTEM

(71) Applicant: KARDION GMBH, Stuttgart (DE)

(72) Inventors: Hardy Baumbach, Stuttgart (DE); Karin Schneider, Herrenberg (DE); Inga Schellenberg, Stuttgart (DE); Martina Budde, Karlsruhe (DE); Thomas Alexander Schlebusch, Renningen (DE)

(73) Assignee: Kardion GmbH, Stuttgart (DE)

( * ) Notice: Subject to any disclaimer, the term of this patent is extended or adjusted under 35 U.S.C. 154(b) by 1083 days.

(21) Appl. No.: 15/734,010

(22) PCT Filed: Jun. 6, 2019

(86) PCT No.: PCT/EP2019/064802
§ 371 (c)(1),
(2) Date: Jul. 9, 2021

(87) PCT Pub. No.: WO2019/234162
PCT Pub. Date: Dec. 12, 2019

(65) Prior Publication Data
US 2021/0346677 A1 Nov. 11, 2021

(30) Foreign Application Priority Data
Jun. 6, 2018 (DE) .......................... 102018208879.9

(51) Int. Cl.
*A61M 60/538* (2021.01)
*A61M 60/178* (2021.01)
(Continued)

(52) U.S. Cl.
CPC ........ *A61M 60/538* (2021.01); *A61M 60/178* (2021.01); *A61M 60/205* (2021.01);
(Continued)

(58) Field of Classification Search
CPC .......................... A61M 60/538; A61M 60/411
(Continued)

(56) References Cited

U.S. PATENT DOCUMENTS

| 3,088,323 | A | 5/1963 | Welkowitz et al. |
| 4,023,562 | A | 5/1977 | Hynecek et al. |

(Continued)

FOREIGN PATENT DOCUMENTS

| CA | 3 122 415 | 7/2020 |
| CN | 1192351 A | 9/1998 |

(Continued)

OTHER PUBLICATIONS

Hertz PH.D et al., "Ultrasonic Engineering in Heart Diagnosis", The American Journal of Cardiology, Jan. 1967, vol. 19, No. 1, pp. 6-17.
(Continued)

*Primary Examiner* — Nadia A Mahmood
(74) *Attorney, Agent, or Firm* — Knobbe, Martens, Olson & Bear, LLP

(57) ABSTRACT

The invention relates to a method for determining a total fluid volume flow (1) in the region of an implanted vascular support system (2), comprising the following steps: a) determining a reference temperature (3) of the fluid, b) determining a motor temperature (4) of an electric motor (5) of the support system (2), c) determining the thermal dissipation loss (6) of the electric motor (5), d) ascertaining the total fluid volume flow (1) using the reference temperature (3), the motor temperature (4), and the thermal dissipation loss (6) of the electric motor (5).

25 Claims, 4 Drawing Sheets

(51) Int. Cl.
*A61M 60/205* (2021.01)
*A61M 60/216* (2021.01)
*A61M 60/411* (2021.01)
*A61M 60/515* (2021.01)
*A61M 60/523* (2021.01)
*A61M 60/546* (2021.01)
*A61M 60/81* (2021.01)
*A61M 60/857* (2021.01)

(52) U.S. Cl.
CPC ........ *A61M 60/216* (2021.01); *A61M 60/411* (2021.01); *A61M 60/515* (2021.01); *A61M 60/523* (2021.01); *A61M 60/546* (2021.01); *A61M 60/81* (2021.01); *A61M 60/857* (2021.01); *A61M 2205/3368* (2013.01); *A61M 2205/50* (2013.01); *A61M 2205/702* (2013.01)

(58) Field of Classification Search
USPC ....................................................... 600/16
See application file for complete search history.

(56) References Cited

U.S. PATENT DOCUMENTS

| | | |
|---|---|---|
| 4,559,952 A | 12/1985 | Angelsen et al. |
| 4,680,730 A | 7/1987 | Omoda |
| 4,781,525 A | 11/1988 | Hubbard et al. |
| 4,888,011 A | 12/1989 | Kung et al. |
| 4,889,131 A | 12/1989 | Salem et al. |
| 4,902,272 A | 2/1990 | Milder et al. |
| 5,045,051 A | 9/1991 | Milder et al. |
| 5,269,811 A | 12/1993 | Hayes |
| 5,289,821 A | 3/1994 | Swartz |
| 5,456,715 A | 10/1995 | Liotta |
| 5,527,159 A | 6/1996 | Bozeman, Jr. et al. |
| 5,581,038 A | 12/1996 | Lampropoulos |
| 5,613,935 A | 3/1997 | Jarvik |
| 5,662,115 A | 9/1997 | Torp |
| 5,676,651 A | 10/1997 | Larson, Jr. et al. |
| 5,720,771 A | 2/1998 | Snell |
| 5,752,976 A | 5/1998 | Duffin et al. |
| 5,766,207 A | 6/1998 | Potter et al. |
| 5,827,203 A | 10/1998 | Nita |
| 5,865,759 A | 2/1999 | Koblanski |
| 5,888,242 A | 3/1999 | Antaki et al. |
| 5,904,708 A | 5/1999 | Goedeke |
| 5,911,685 A | 6/1999 | Siess et al. |
| 5,964,694 A | 10/1999 | Siess et al. |
| 5,980,465 A | 11/1999 | Elgas |
| 6,007,478 A | 12/1999 | Siess et al. |
| 6,024,704 A | 2/2000 | Meador et al. |
| 6,053,873 A | 4/2000 | Govari et al. |
| 6,167,765 B1 | 1/2001 | Weitzel |
| 6,176,822 B1 | 1/2001 | Nix et al. |
| 6,183,412 B1 | 2/2001 | Benkowsi et al. |
| 6,185,460 B1 | 2/2001 | Thompson |
| 6,190,324 B1 | 2/2001 | Kieval et al. |
| 6,210,318 B1 | 4/2001 | Lederman |
| 6,231,498 B1 | 5/2001 | Pfeiffer et al. |
| 6,245,007 B1 | 6/2001 | Bedingham et al. |
| 6,314,322 B1 | 11/2001 | Rosenberg |
| 6,351,048 B1 | 2/2002 | Schob et al. |
| 6,398,734 B1 | 6/2002 | Cimochowski et al. |
| 6,432,136 B1 | 8/2002 | Weiss et al. |
| 6,438,409 B1 | 8/2002 | Malik et al. |
| 6,512,949 B1 | 1/2003 | Combs et al. |
| 6,530,876 B1 | 3/2003 | Spence |
| 6,540,658 B1 | 4/2003 | Fasciano et al. |
| 6,540,659 B1 | 4/2003 | Milbocker |
| 6,561,975 B1 | 5/2003 | Pool et al. |
| 6,579,257 B1 | 6/2003 | Elgas et al. |
| 6,602,182 B1 | 8/2003 | Milbocker |
| 6,605,032 B2 | 8/2003 | Benkowsi et al. |
| 6,652,447 B2 | 11/2003 | Benkowsi et al. |
| 6,731,976 B2 | 5/2004 | Penn et al. |
| 6,879,126 B2 | 4/2005 | Paden et al. |
| 6,912,423 B2 | 6/2005 | Ley et al. |
| 6,949,066 B2 | 9/2005 | Bearnson et al. |
| 6,984,201 B2 | 1/2006 | Khaghani et al. |
| 7,010,954 B2 | 3/2006 | Siess |
| 7,022,100 B1 | 4/2006 | Aboul-Hosn et al. |
| 7,024,244 B2 | 4/2006 | Muhlenberg et al. |
| 7,070,555 B2 | 7/2006 | Siess |
| 7,083,588 B1 | 8/2006 | Shmulewitz et al. |
| 7,138,776 B1 | 11/2006 | Gauthier et al. |
| 7,160,243 B2 | 1/2007 | Medvedev |
| 7,175,588 B2 | 2/2007 | Morello |
| 7,177,681 B2 | 2/2007 | Xhu |
| 7,238,151 B2 | 7/2007 | Frazier |
| 7,396,327 B2 | 7/2008 | Morello |
| 7,513,864 B2 | 4/2009 | Kantrowitz et al. |
| 7,520,850 B2 | 4/2009 | Brockway |
| 7,527,599 B2 | 5/2009 | Hickey |
| 7,591,777 B2 | 9/2009 | LaRose |
| 7,744,560 B2 | 6/2010 | Struble |
| 7,794,384 B2 | 9/2010 | Sugiura et al. |
| 7,819,916 B2 | 10/2010 | Yaegashi |
| 7,850,593 B2 | 12/2010 | Vincent et al. |
| 7,850,594 B2 | 12/2010 | Sutton et al. |
| 7,856,335 B2 | 12/2010 | Morello et al. |
| 7,862,501 B2 | 1/2011 | Woodward et al. |
| 7,951,062 B2 | 5/2011 | Morello |
| 7,951,129 B2 | 5/2011 | Chinchoy |
| 7,963,905 B2 | 6/2011 | Salmonsen et al. |
| 7,988,728 B2 | 8/2011 | Ayre |
| 8,075,472 B2 | 12/2011 | Zilbershlag et al. |
| 8,190,390 B2 | 5/2012 | Morello et al. |
| 8,211,028 B2 | 7/2012 | Karamanoglu et al. |
| 8,303,482 B2 | 11/2012 | Schima et al. |
| 8,323,173 B2 | 12/2012 | Benkowsi et al. |
| 8,435,182 B1 | 5/2013 | Tamura |
| 8,449,444 B2 | 5/2013 | Poirier |
| 8,545,380 B2 | 10/2013 | Farnan et al. |
| 8,585,572 B2 | 11/2013 | Mehmanesh |
| 8,591,393 B2 | 11/2013 | Walters et al. |
| 8,594,790 B2 | 11/2013 | Kjellstrom et al. |
| 8,622,949 B2 | 1/2014 | Zafirelis et al. |
| 8,657,733 B2 | 2/2014 | Ayre et al. |
| 8,657,875 B2 | 2/2014 | Kung et al. |
| 8,715,151 B2 | 5/2014 | Poirier |
| 8,747,293 B2 | 6/2014 | Arndt et al. |
| 8,849,398 B2 | 9/2014 | Evans |
| 8,864,643 B2 | 10/2014 | Reichenbach et al. |
| 8,864,644 B2 | 10/2014 | Yomtov |
| 8,876,685 B2 | 11/2014 | Crosby et al. |
| 8,882,477 B2 | 11/2014 | Fritz, IV et al. |
| 8,888,728 B2 | 11/2014 | Aboul-Hosn et al. |
| 8,897,873 B2 | 11/2014 | Schima et al. |
| 8,903,492 B2 | 12/2014 | Soykan et al. |
| 9,091,271 B2 | 7/2015 | Bourque |
| 9,297,735 B2 | 3/2016 | Graichen et al. |
| 9,308,305 B2 | 4/2016 | Chen et al. |
| 9,345,824 B2 | 5/2016 | Mohl et al. |
| 9,371,826 B2 | 6/2016 | Yanai et al. |
| 9,427,508 B2 | 8/2016 | Reyes et al. |
| 9,474,840 B2 | 10/2016 | Siess |
| 9,492,601 B2 | 11/2016 | Casas et al. |
| 9,511,179 B2 | 12/2016 | Casas et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,566,374 B2 | 2/2017 | Spence et al. |
| 9,636,442 B2 | 5/2017 | Karmon et al. |
| 9,656,010 B2 | 5/2017 | Burke |
| 9,669,142 B2 | 6/2017 | Spanier et al. |
| 9,669,144 B2 | 6/2017 | Spanier et al. |
| 9,694,123 B2 | 7/2017 | Bourque et al. |
| 9,713,701 B2 | 7/2017 | Sarkar et al. |
| 9,744,282 B2 | 8/2017 | Rosenberg et al. |
| 9,789,236 B2 | 10/2017 | Bonde |
| 9,833,550 B2 | 12/2017 | Siess |
| 9,848,899 B2 | 12/2017 | Sliwa et al. |
| 9,849,224 B2 | 12/2017 | Angwin et al. |
| 9,878,087 B2 | 1/2018 | Richardson et al. |

(56) References Cited

U.S. PATENT DOCUMENTS

| | | |
|---|---|---|
| 9,943,236 B2 | 4/2018 | Bennett et al. |
| 9,950,102 B2 | 4/2018 | Spence et al. |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |
| 10,029,037 B2 | 7/2018 | Muller et al. |
| 10,052,420 B2 | 8/2018 | Medvedev et al. |
| 10,279,093 B2 | 5/2019 | Reichenbach et al. |
| 10,322,217 B2 | 6/2019 | Spence |
| 10,342,906 B2 | 7/2019 | D'Ambrosio et al. |
| 10,350,342 B2 | 7/2019 | Thomas et al. |
| 10,357,598 B2 | 7/2019 | Aboul-Hosn et al. |
| 10,376,162 B2 | 8/2019 | Edelman et al. |
| 10,413,651 B2 | 9/2019 | Yomtov et al. |
| 10,426,879 B2 | 10/2019 | Farnan |
| 10,449,275 B2 | 10/2019 | Corbett |
| 10,500,322 B2 | 12/2019 | Karch |
| 10,525,178 B2 | 1/2020 | Zeng |
| 10,549,020 B2 | 2/2020 | Spence et al. |
| 10,561,771 B2 | 2/2020 | Heilman et al. |
| 10,561,772 B2 | 2/2020 | Schumacher |
| 10,561,773 B2 | 2/2020 | Ferrari et al. |
| 10,632,241 B2 | 4/2020 | Schenck et al. |
| 10,660,998 B2 | 5/2020 | Hodges |
| 10,668,195 B2 | 6/2020 | Flores |
| 10,732,583 B2 | 8/2020 | Rudser |
| 10,857,275 B2 | 12/2020 | Granegger |
| 10,864,308 B2 | 12/2020 | Muller et al. |
| 11,027,114 B2 | 6/2021 | D'Ambrosio et al. |
| RE48,649 E | 7/2021 | Siess |
| 11,067,085 B2 | 7/2021 | Granegger et al. |
| 11,120,908 B2 | 9/2021 | Agnello et al. |
| 11,131,968 B2 | 9/2021 | Rudser |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,185,682 B2 | 11/2021 | Farnan |
| 11,191,945 B2 | 12/2021 | Siess et al. |
| 11,197,618 B2 | 12/2021 | Edelman et al. |
| 11,217,344 B2 | 1/2022 | Agnello |
| 11,235,139 B2 | 2/2022 | Kudlik |
| 11,241,572 B2 | 2/2022 | Dague et al. |
| 11,273,299 B2 | 3/2022 | Wolman et al. |
| 11,285,310 B2 | 3/2022 | Curran et al. |
| 11,285,311 B2 | 3/2022 | Siess et al. |
| 11,298,524 B2 | 4/2022 | El Katerji et al. |
| 11,311,711 B2 | 4/2022 | Casas et al. |
| 11,316,679 B2 | 4/2022 | Agnello |
| 11,320,382 B2 | 5/2022 | Aikawa |
| 11,324,395 B2 | 5/2022 | Banik et al. |
| 11,331,082 B2 | 5/2022 | Itoh et al. |
| 11,337,724 B2 | 5/2022 | Masubuchi et al. |
| 11,338,125 B2 | 5/2022 | Liu et al. |
| 11,351,356 B2 | 6/2022 | Mohl |
| 11,351,357 B2 | 6/2022 | Mohl |
| 11,351,358 B2 | 6/2022 | Nix et al. |
| 11,357,438 B2 | 6/2022 | Stewart et al. |
| 11,357,968 B2 | 6/2022 | El Katerji et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,444 B2 | 8/2022 | Nix et al. |
| 11,413,445 B2 | 8/2022 | Brown et al. |
| 11,420,041 B2 | 8/2022 | Karch |
| 11,439,806 B2 | 9/2022 | Kimball et al. |
| 11,446,481 B2 | 9/2022 | Wolman et al. |
| 11,478,629 B2 | 10/2022 | Harjes et al. |
| 11,517,740 B2 | 12/2022 | Agarwa et al. |
| 11,521,723 B2 | 12/2022 | Liu et al. |
| 11,524,165 B2 | 12/2022 | Tan et al. |
| 11,527,322 B2 | 12/2022 | Agnello et al. |
| 11,529,062 B2 | 12/2022 | Moyer et al. |
| 11,554,260 B2 | 1/2023 | Reyes et al. |
| 11,572,879 B2 | 2/2023 | Mohl |
| 11,574,741 B2 | 2/2023 | Tan et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,587,337 B2 | 2/2023 | Lemay et al. |
| 11,590,337 B2 | 2/2023 | Granegger et al. |
| 11,622,695 B1 | 4/2023 | Adriola et al. |
| 11,628,293 B2 | 4/2023 | Gandhi et al. |
| 11,639,722 B2 | 5/2023 | Medvedev et al. |
| 11,648,386 B2 | 5/2023 | Poirer |
| 11,653,841 B2 | 5/2023 | Reyes et al. |
| 11,666,746 B2 | 6/2023 | Ferrari et al. |
| 11,668,321 B2 | 6/2023 | Richert et al. |
| 11,674,517 B2 | 6/2023 | Mohl |
| 11,676,718 B2 | 6/2023 | Agnello et al. |
| 11,684,276 B2 | 6/2023 | Cros et al. |
| 11,684,769 B2 | 6/2023 | Harjes et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,707,617 B2 | 7/2023 | Reyes et al. |
| 11,712,167 B2 | 8/2023 | Medvedev et al. |
| 11,754,077 B1 | 9/2023 | Mohl |
| D1,001,145 S | 10/2023 | Lussier et al. |
| D1,001,146 S | 10/2023 | Lussier et al. |
| 11,771,885 B2 | 10/2023 | Liu et al. |
| 11,779,234 B2 | 10/2023 | Harjes et al. |
| 11,781,551 B2 | 10/2023 | Yanai et al. |
| 11,790,487 B2 | 10/2023 | Barbato et al. |
| 11,793,994 B2 | 10/2023 | Josephy et al. |
| 11,806,116 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,818,782 B2 | 11/2023 | Doudian et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,837,364 B2 | 12/2023 | Lee et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,864,878 B2 | 1/2024 | Duval et al. |
| 11,872,384 B2 | 1/2024 | Cotter |
| 11,883,207 B2 | 1/2024 | El Katerji et al. |
| D1,014,552 S | 2/2024 | Lussier et al. |
| 11,890,082 B2 | 2/2024 | Cros et al. |
| 11,896,199 B2 | 2/2024 | Lent et al. |
| 11,900,660 B2 | 2/2024 | Saito et al. |
| 11,903,657 B2 | 2/2024 | Geric et al. |
| 11,906,411 B2 | 2/2024 | Graichen et al. |
| 11,911,550 B2 | 2/2024 | Itamochi et al. |
| D1,017,634 S | 3/2024 | Lussier et al. |
| D1,017,699 S | 3/2024 | Moore et al. |
| 11,923,078 B2 | 3/2024 | Fallen et al. |
| 11,923,093 B2 | 3/2024 | Moffitt et al. |
| 11,925,794 B2 | 3/2024 | Malkin et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,986,274 B2 | 5/2024 | Edelman |
| 12,017,076 B2 | 6/2024 | Tan et al. |
| 12,023,476 B2 | 7/2024 | Tuval et al. |
| 12,029,891 B2 | 7/2024 | Siess et al. |
| 12,059,559 B2 | 8/2024 | Muller et al. |
| D1,043,730 S | 9/2024 | Lussier et al. |
| D1,043,731 S | 9/2024 | Lussier et al. |
| 12,076,544 B2 | 9/2024 | Siess et al. |
| 12,097,016 B2 | 9/2024 | Goldvasser |
| 12,102,815 B2 | 10/2024 | Dhaliwal et al. |
| 12,144,650 B2 | 11/2024 | Spanier et al. |
| 12,144,976 B2 | 11/2024 | Baumbach et al. |
| 2001/0016686 A1 | 8/2001 | Okada et al. |

(56) References Cited

U.S. PATENT DOCUMENTS

| | | |
|---|---|---|
| 2001/0037093 A1 | 11/2001 | Benkowski et al. |
| 2001/0039828 A1 | 11/2001 | Shin et al. |
| 2002/0022785 A1 | 2/2002 | Romano |
| 2002/0082585 A1 | 6/2002 | Carroll et al. |
| 2002/0147495 A1 | 10/2002 | Petroff |
| 2002/0151761 A1 | 10/2002 | Viole et al. |
| 2003/0069465 A1 | 4/2003 | Benkowski et al. |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2003/0199727 A1 | 10/2003 | Burke |
| 2004/0022640 A1 | 2/2004 | Siess et al. |
| 2004/0044266 A1 | 3/2004 | Siess et al. |
| 2004/0065143 A1 | 4/2004 | Husher |
| 2004/0130009 A1 | 7/2004 | Tangpuz |
| 2004/0167376 A1 | 8/2004 | Peters et al. |
| 2004/0167410 A1 | 8/2004 | Hettrick |
| 2004/0225177 A1 | 11/2004 | Coleman et al. |
| 2004/0241019 A1 | 12/2004 | Goldowsky |
| 2004/0260346 A1 | 12/2004 | Overall et al. |
| 2005/0001324 A1 | 1/2005 | Dunn |
| 2005/0019167 A1 | 1/2005 | Nusser et al. |
| 2005/0107658 A1 | 5/2005 | Brockway |
| 2005/0126268 A1 | 6/2005 | Ouriev et al. |
| 2005/0267322 A1 | 12/2005 | LaRose |
| 2006/0030809 A1 | 2/2006 | Barzilay et al. |
| 2006/0108697 A1 | 5/2006 | Wang |
| 2006/0108901 A1 | 5/2006 | Mao-Chin |
| 2006/0122583 A1 | 6/2006 | Pesach et al. |
| 2006/0196277 A1 | 9/2006 | Allen et al. |
| 2006/0229488 A1 | 10/2006 | Ayre et al. |
| 2006/0287600 A1 | 12/2006 | McEowen |
| 2006/0287604 A1 | 12/2006 | Hickey |
| 2007/0060787 A1 | 3/2007 | Peters et al. |
| 2007/0069354 A1 | 3/2007 | Dangelmaier |
| 2007/0073352 A1 | 3/2007 | Euler et al. |
| 2007/0088214 A1 | 4/2007 | Shuros et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2007/0299325 A1 | 12/2007 | Farrell et al. |
| 2008/0015517 A1 | 1/2008 | Geistert et al. |
| 2008/0082005 A1 | 4/2008 | Stern et al. |
| 2008/0091239 A1 | 4/2008 | Johansson et al. |
| 2008/0097595 A1 | 4/2008 | Gabbay |
| 2008/0102096 A1 | 5/2008 | Molin et al. |
| 2008/0108901 A1 | 5/2008 | Baba et al. |
| 2008/0108930 A1 | 5/2008 | Weitzel et al. |
| 2008/0133006 A1 | 6/2008 | Crosby et al. |
| 2008/0146996 A1* | 6/2008 | Smisson ............ A61M 1/0281 604/113 |
| 2008/0210016 A1 | 9/2008 | Zwirn et al. |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0306328 A1 | 12/2008 | Ercolani |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0131765 A1 | 5/2009 | Roschak et al. |
| 2009/0204163 A1 | 8/2009 | Shuros et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0172505 A1 | 7/2011 | Kim |
| 2011/0184301 A1 | 7/2011 | Holmstrom |
| 2011/0218435 A1 | 9/2011 | Srinivasan et al. |
| 2011/0230068 A1 | 9/2011 | Pahl |
| 2012/0022645 A1 | 1/2012 | Burke |
| 2012/0084024 A1 | 4/2012 | Norcross, Jr. |
| 2012/0150089 A1 | 6/2012 | Penka et al. |
| 2012/0203476 A1 | 8/2012 | Dam |
| 2012/0245404 A1 | 9/2012 | Smith |
| 2012/0247200 A1 | 10/2012 | Ahonen et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0066141 A1 | 3/2013 | Doerr et al. |
| 2013/0066142 A1 | 3/2013 | Doerr et al. |
| 2013/0072846 A1 | 3/2013 | Heide et al. |
| 2013/0116575 A1 | 5/2013 | Mickle et al. |
| 2013/0144379 A1 | 6/2013 | Najafi et al. |
| 2013/0289334 A1 | 10/2013 | Badstibner |
| 2013/0289376 A1 | 10/2013 | Lang |
| 2013/0303831 A1 | 11/2013 | Evans |
| 2013/0304404 A1 | 11/2013 | Dam |
| 2014/0013852 A1 | 1/2014 | Brown et al. |
| 2014/0030122 A1 | 1/2014 | Ozaki |
| 2014/0100414 A1 | 4/2014 | Tamez et al. |
| 2014/0114202 A1 | 4/2014 | Hein et al. |
| 2014/0128659 A1 | 5/2014 | Heuring et al. |
| 2014/0200389 A1 | 7/2014 | Yanai et al. |
| 2014/0243688 A1 | 8/2014 | Caron et al. |
| 2014/0275720 A1 | 9/2014 | Ferrari |
| 2014/0275727 A1 | 9/2014 | Bonde |
| 2014/0296677 A1 | 10/2014 | McEowen |
| 2014/0303426 A1 | 10/2014 | Kerkhoffs et al. |
| 2014/0342203 A1 | 11/2014 | Elian |
| 2015/0032007 A1 | 1/2015 | Ottevanger et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0174307 A1 | 6/2015 | Eckman et al. |
| 2015/0190092 A1 | 7/2015 | Mori |
| 2015/0250935 A1 | 9/2015 | Anderson et al. |
| 2015/0273184 A1 | 10/2015 | Scott et al. |
| 2015/0290372 A1 | 10/2015 | Muller et al. |
| 2015/0306290 A1 | 10/2015 | Rosenberg et al. |
| 2015/0306291 A1 | 10/2015 | Bonde et al. |
| 2015/0307344 A1 | 10/2015 | Ernst |
| 2015/0327921 A1 | 11/2015 | Govari |
| 2015/0335804 A1 | 11/2015 | Marseille et al. |
| 2015/0365738 A1 | 12/2015 | Purvis et al. |
| 2016/0000983 A1 | 1/2016 | Mohl et al. |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0045165 A1 | 2/2016 | Braido et al. |
| 2016/0095968 A1 | 4/2016 | Rudser |
| 2016/0101230 A1 | 4/2016 | Ochsner et al. |
| 2016/0144166 A1 | 5/2016 | Decré al. |
| 2016/0151553 A1 | 6/2016 | Bonde |
| 2016/0166747 A1 | 6/2016 | Frazier et al. |
| 2016/0213828 A1 | 7/2016 | Sievers |
| 2016/0250399 A1 | 9/2016 | Tiller et al. |
| 2016/0278856 A1 | 9/2016 | Panescu |
| 2016/0302672 A1 | 10/2016 | Kuri |
| 2016/0317043 A1 | 11/2016 | Campo |
| 2016/0338629 A1 | 11/2016 | Doerr |
| 2017/0010144 A1 | 1/2017 | Lenner et al. |
| 2017/0021070 A1 | 1/2017 | Petersen |
| 2017/0049945 A1 | 2/2017 | Halvorsen et al. |
| 2017/0086780 A1 | 3/2017 | Sokulin et al. |
| 2017/0098491 A1 | 4/2017 | Ziaie et al. |

(56) References Cited

U.S. PATENT DOCUMENTS

| | | |
|---|---|---|
| 2017/0112985 A1 | 4/2017 | Yomtov |
| 2017/0128646 A1 | 5/2017 | Karch |
| 2017/0136164 A1 | 5/2017 | Yeatts |
| 2017/0202575 A1 | 7/2017 | Stanfield et al. |
| 2017/0224279 A1 | 8/2017 | Cahan et al. |
| 2017/0239407 A1 | 8/2017 | Hayward |
| 2017/0258980 A1 | 9/2017 | Katsuki et al. |
| 2017/0348470 A1 | 12/2017 | D'Ambrosio et al. |
| 2017/0354812 A1 | 12/2017 | Callaghan et al. |
| 2018/0064860 A1 | 3/2018 | Nunez et al. |
| 2018/0078159 A1 | 3/2018 | Edelman et al. |
| 2018/0093070 A1 | 4/2018 | Cottone |
| 2018/0110910 A1 | 4/2018 | Rodemerk et al. |
| 2018/0199635 A1 | 7/2018 | Longinotti-Buitoni et al. |
| 2018/0250457 A1 | 9/2018 | Morello et al. |
| 2018/0256796 A1 | 9/2018 | Hansen |
| 2018/0256800 A1 | 9/2018 | Conyers et al. |
| 2018/0264182 A1 | 9/2018 | Spanier et al. |
| 2018/0280598 A1 | 10/2018 | Curran et al. |
| 2018/0316209 A1 | 11/2018 | Gliner |
| 2018/0326131 A1 | 11/2018 | Muller et al. |
| 2018/0333059 A1 | 11/2018 | Casas |
| 2018/0353667 A1 | 12/2018 | Moyer et al. |
| 2018/0369469 A1 | 12/2018 | Le Duc De Lillers et al. |
| 2019/0001038 A1 | 1/2019 | Yomtov et al. |
| 2019/0054223 A1 | 2/2019 | Frazier et al. |
| 2019/0083690 A1 | 3/2019 | Siess et al. |
| 2019/0192752 A1 | 6/2019 | Tiller et al. |
| 2019/0192753 A1 | 6/2019 | Liu et al. |
| 2019/0209755 A1 | 7/2019 | Nix et al. |
| 2019/0209758 A1 | 7/2019 | Tuval et al. |
| 2019/0216995 A1 | 7/2019 | Kapur et al. |
| 2019/0217002 A1 | 7/2019 | Urakabe |
| 2019/0223877 A1 | 7/2019 | Nitzen et al. |
| 2019/0240680 A1 | 8/2019 | Hayakawa |
| 2019/0254543 A1 | 8/2019 | Hartholt et al. |
| 2019/0282741 A1 | 9/2019 | Franano et al. |
| 2019/0282744 A1 | 9/2019 | D'Ambrosio et al. |
| 2019/0351117 A1 | 11/2019 | Cambronne et al. |
| 2019/0351118 A1 | 11/2019 | Graichen et al. |
| 2020/0016309 A1 | 1/2020 | Kallenbach et al. |
| 2020/0038567 A1 | 2/2020 | Siess et al. |
| 2020/0060559 A1 | 2/2020 | Edelman et al. |
| 2020/0069857 A1 | 3/2020 | Schwammenthal et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0253583 A1 | 8/2020 | Brisken et al. |
| 2020/0312450 A1 | 10/2020 | Agnello et al. |
| 2021/0268264 A1 | 9/2021 | Stotz |
| 2021/0290087 A1 | 9/2021 | Schlebusch |
| 2021/0290930 A1 | 9/2021 | Kasel |
| 2021/0290933 A1 | 9/2021 | Stotz |
| 2021/0339002 A1 | 11/2021 | Schlebusch et al. |
| 2021/0339004 A1 | 11/2021 | Schlebusch et al. |
| 2021/0346674 A1 | 11/2021 | Baumbach et al. |
| 2021/0346675 A1 | 11/2021 | Schlebusch et al. |
| 2021/0346676 A1 | 11/2021 | Schlebusch et al. |
| 2021/0346678 A1 | 11/2021 | Baumbach et al. |
| 2021/0378523 A1 | 12/2021 | Budde |
| 2021/0379359 A1 | 12/2021 | Schellenberg |
| 2021/0379360 A1 | 12/2021 | Schellenberg |
| 2021/0393944 A1 | 12/2021 | Wenning |
| 2022/0016411 A1 | 1/2022 | Winterwerber |
| 2022/0032032 A1 | 2/2022 | Schlebusch et al. |
| 2022/0032036 A1 | 2/2022 | Baumbach et al. |
| 2022/0039669 A1 | 2/2022 | Schlebusch et al. |
| 2022/0047173 A1 | 2/2022 | Stotz et al. |
| 2022/0050037 A1 | 2/2022 | Stotz et al. |
| 2022/0072298 A1 | 3/2022 | Spanier et al. |
| 2022/0076807 A1 | 3/2022 | Agnello |
| 2022/0079457 A1 | 3/2022 | Tuval et al. |
| 2022/0105339 A1 | 4/2022 | Nix et al. |
| 2022/0126085 A1 | 4/2022 | Farnan |
| 2022/0126086 A1 | 4/2022 | Schlebusch et al. |
| 2022/0142462 A1 | 5/2022 | Douk et al. |
| 2022/0161019 A1 | 5/2022 | Mitze et al. |
| 2022/0361762 A1 | 11/2022 | Lalancette |
| 2023/0173250 A1 | 6/2023 | Stigloher |
| 2023/0191141 A1 | 6/2023 | Wenning et al. |
| 2024/0011808 A1 | 1/2024 | Winzer et al. |
| 2024/0074828 A1 | 3/2024 | Wenning |
| 2024/0245902 A1 | 7/2024 | Schlebusch et al. |

FOREIGN PATENT DOCUMENTS

| | | |
|---|---|---|
| CN | 1222862 A | 7/1999 |
| CN | 1202871 C | 5/2005 |
| CN | 1661338 A | 8/2005 |
| CN | 101128168 | 2/2008 |
| CN | 101208045 | 6/2008 |
| CN | 101214158 | 7/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201658687 | 12/2010 |
| CN | 102421372 | 4/2012 |
| CN | 102803923 | 11/2012 |
| CN | 103328018 | 9/2013 |
| CN | 103857326 | 6/2014 |
| CN | 103957957 | 7/2014 |
| CN | 104105449 | 10/2014 |
| CN | 104188687 | 12/2014 |
| CN | 106104229 | 11/2016 |
| CN | 106333707 | 1/2017 |
| CN | 206007680 | 3/2017 |
| CN | 107530479 | 1/2018 |
| CN | 107632167 | 1/2018 |
| CN | 109939282 | 6/2019 |
| CN | 209790495 | 12/2019 |
| CN | 210020563 | 2/2020 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 794 411 | 9/1997 |
| EP | 0 916 359 | 5/1999 |
| EP | 1 062 959 | 12/2000 |
| EP | 1 339 443 | 11/2001 |
| EP | 1 011 803 | 9/2004 |
| EP | 1 354 606 | 6/2006 |
| EP | 2 143 385 | 1/2010 |
| EP | 2 175 770 | 4/2010 |

(56) References Cited

FOREIGN PATENT DOCUMENTS

| | | |
|---|---|---|
| EP | 2 187 807 | 6/2012 |
| EP | 2 570 143 | 3/2013 |
| EP | 2 401 003 | 10/2013 |
| EP | 1 871 441 | 11/2014 |
| EP | 2 859 911 | 4/2015 |
| EP | 2 213 227 | 8/2016 |
| EP | 2 835 141 | 8/2016 |
| EP | 3 088 016 | 11/2016 |
| EP | 2 585 129 | 3/2017 |
| EP | 2 945 661 | 11/2017 |
| EP | 2 136 861 | 12/2017 |
| EP | 3 020 426 | 12/2017 |
| EP | 3 287 154 | 2/2018 |
| EP | 3 205 359 | 8/2018 |
| EP | 3 205 360 | 8/2018 |
| EP | 3 389 738 | 8/2019 |
| EP | 2 505 090 | 12/2019 |
| EP | 3 668 560 | 6/2020 |
| EP | 3 720 520 | 10/2020 |
| EP | 3 753 594 | 12/2020 |
| EP | 3 357 523 | 1/2021 |
| EP | 3 490 628 | 2/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 3 131 600 | 6/2021 |
| EP | 3 131 615 | 6/2021 |
| EP | 3 463 505 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 651 822 | 3/2022 |
| EP | 3 689 389 | 3/2022 |
| EP | 3 737 436 | 3/2022 |
| EP | 3 972 661 | 3/2022 |
| EP | 3 984 589 | 4/2022 |
| EP | 3 654 006 | 5/2022 |
| EP | 3 737 310 | 7/2022 |
| EP | 2 999 400 | 8/2022 |
| EP | 3 711 788 | 8/2022 |
| EP | 3 694 573 | 9/2022 |
| EP | 3 600 477 | 10/2022 |
| EP | 3 897 768 | 10/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 685 562 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| EP | 3 793 674 | 10/2024 |
| EP | 3 618 885 | 11/2024 |
| EP | 4 034 221 | 11/2024 |
| ES | 2 913 485 | 6/2022 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-523110 | 8/2019 |
| JP | 2020-072985 | 5/2020 |
| WO | WO 92/015239 | 9/1992 |
| WO | WO 98/043688 | 10/1998 |
| WO | WO 00/033047 | 6/2000 |
| WO | WO 2006/122001 | 11/2006 |
| WO | WO 2010/142286 | 12/2010 |
| WO | WO 2010/143272 | 12/2010 |
| WO | WO 2012/018917 | 2/2012 |
| WO | WO 2012/112378 | 8/2012 |
| WO | WO 2013/160443 | 10/2013 |

(56) References Cited

FOREIGN PATENT DOCUMENTS

| WO | WO 2014/042925 | 3/2014 |
|---|---|---|
| WO | WO 2014/141284 | 9/2014 |
| WO | WO 2014/165635 | 10/2014 |
| WO | WO 2015/085220 | 6/2015 |
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/087717 | 5/2017 |
| WO | WO 2017/106190 | 6/2017 |
| WO | WO 2017/117215 | 7/2017 |
| WO | WO 2017/147291 | 8/2017 |
| WO | WO 2017/214118 | 12/2017 |
| WO | WO 2018/005228 | 1/2018 |
| WO | WO 2018/048800 | 3/2018 |
| WO | WO 2018/109038 | 6/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/078723 | 4/2019 |
| WO | WO 2019/126721 | 6/2019 |
| WO | WO 2019/137911 | 7/2019 |
| WO | WO 2019/193604 | 10/2019 |
| WO | WO 2019/219883 | 11/2019 |
| WO | WO 2019/229210 | 12/2019 |
| WO | WO 2019/229220 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |
| WO | WO 2020/243756 | 12/2020 |
| WO | WO 2022/074136 | 4/2022 |
| WO | WO 2022/109590 | 5/2022 |
| WO | WO 2022/173970 | 8/2022 |
| WO | WO 2023/049813 | 3/2023 |

OTHER PUBLICATIONS

International Search Report and Written Opinion received in PCT Application No. PCT/EP2019/064802, dated Aug. 27, 2019 in 10 pages.

International Preliminary Report on Patentability and Written Opinion received in PCT Application No. PCT/EP2019/064802, dated Dec. 17, 2020 in 7 pages.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Atkinson et al., "Pulse-Doppler Ultrasound and Its Clinical Application", The Yale Journal of Biology and Medicine, 1977, vol. 50, pp. 367-373.

Leguy et al., "Assessment of Blood Volume Flow in Slightly Curved Arteries from a Single Velocity Profile", Journal of Biomechanics, 2009, pp. 1664-1672.

Lombardi et al., "Flow Rate Profiler: an instrument to measure blood velocity profiles", Ultrasonics, 2001, vol. 39, pp. 143-150.

Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.

"Understanding Hot-Wire Anemometry", Advanced Thermal Solutions, Inc., 2007, pp. 13-17.

Vieli, A., "Doppler Flow Determination", BJA: British Journal of Anaesthesia, 1988, vol. 60, pp. 107S-112S.

Yuanyuan et al., "Characteristics Analysis for Doppler Ultrasound Blood Flow Signals", China Medical Device Information, 5(1), Feb. 28, 1999, pp. 36-42.

Zhang, Dabiao et al., "Design of Microwave Velocity and Distance Monitor System", Instrument Technique and Sensor, Hebei Normal University, Apr. 25, 2004, pp. 3.

HeartMate 3™ Left Ventricular Assist System, Instructions for Use, Thoratec Corporation, Aug. 2017, pp. 536. [Uploaded in 3 parts].

\* cited by examiner

SYSTEMS AND METHODS FOR DETERMINING A TOTAL BLOOD VOLUME FLOW IN A CARDIAC SUPPORT SYSTEM AND VASCULAR SUPPORT SYSTEM

BACKGROUND

Field

The invention relates to a method for determining a total fluid volume flow in the region of an implanted vascular support system, a processing unit, and an implantable vascular support system. The invention is in particular used in (fully) implanted left-heart support systems (LVAD).

Description of the Related Art

Implanted left-heart support systems (LVAD) mainly exist in two design variants. On the one hand, there are (percutaneous) minimally invasive left-heart support systems. The second variant are left-heart support systems invasively implanted under the chest opening. The variant according to the first variant conveys blood directly from the left ventricle into the aorta since the (percutaneous) minimally invasive left-heart support system is positioned centrally in the aortic valve. The second variant conveys the blood from the left ventricle via a bypass tube into the aorta.

The task of a cardiac support system is to convey blood. In this respect, the so-called heart-time volume (HTV, usually indicated in liters per minute) is highly clinically relevant. In other words, the heart-time volume in this case relates to the total volume flow of blood (from a ventricle), in particular from the left ventricle, to the aorta. Correspondingly clear is the attempt to collect this parameter as a measured value during operation of a cardiac support system.

Depending on the level of support, which describes the proportion of the volume flow conveyed by a conveying means, such as a pump of the support system, to the total volume flow of blood from the ventricle to the aorta, a certain volume flow reaches the aorta via the physiological path through the aortic valve. The heart-time volume or the total volume flow ($Q_{HTV}$) from the ventricle to the aorta is therefore usually the sum of the pump volume flow ($Q_p$) and the aortic valve volume flow ($Q_a$).

An established method for determining the heart-time volume ($Q_{HTV}$) in the clinical setting is the use of dilution methods, which, however, all rely on a transcutaneously inserted catheter and therefore can only provide heart-time volume measurement data during cardiac surgery. An established method for measuring the pump volume flow ($Q_p$) is the correlation of the operating parameters of the support system, predominantly the electrical power consumption, possibly supplemented by further physiological parameters, such as the blood pressure. The integration of dedicated ultrasound measurement technology into a support system has also already been proposed.

A (fully) implanted detection of the heart-time volume, i.e., of $Q_{HTV}$, in particular by the support system itself, has not yet been proposed or realized. Fully implanted means, in particular, that the means required for the detection are completely located in the body of the patient and remain there. This makes it possible to detect the heart-time volume even outside of cardiac surgery.

SUMMARY

The object of the invention is to specify an improved method for determining a total fluid volume flow in the region of an implanted vascular support system and to create an improved implantable vascular support system.

In particular, it is an object of the invention to specify a method for determining a total fluid volume flow in the region of an implanted vascular support system and to create an implantable vascular support system by means of which a total fluid volume flow in a blood flow region can be determined in a human or animal body, in which the vascular support system is implanted or arranged.

This object is achieved by the method specified herein and the implantable vascular support system specified herein.

A method for determining a total fluid volume flow in the region of an implanted vascular support system comprises the following steps:

a) determining a reference temperature of the fluid,
b) determining a motor temperature of an electric motor of the support system,
c) determining the thermal dissipation loss of the electric motor,
d) ascertaining the total fluid volume flow using the reference temperature, the motor temperature, and the thermal dissipation loss of the electric motor.

The vascular support system is preferably a cardiac support system, particularly preferably a ventricular support system. The "total volume flow" in particular refers to the total volume flow through a blood vessel or through a cross section of the blood vessel. The blood vessel is, for example, the aorta, in particular in the case of a left-heart support system, or the common trunk (*Truncus pulmonalis*) into the two pulmonary arteries, in particular in the case of a right-heart support system, preferably the aorta. The method preferably serves to determine a total fluid volume flow from a ventricle of a heart, in particular from a (left) ventricle of a heart, to the aorta in the region of a (fully) implanted, (left) ventricular (heart) support system. The fluid is regularly blood. The support system is preferably arranged at the exit of the left ventricle of the heart or the left heart chamber. The support system is particularly preferably arranged in the aortic valve position.

The method is in particular suitable for determining the total heart-time volume (HTV, formula symbol $Q_{HTV}$) of a patient, in particular with (fully) implanted left ventricular heart support system (LVAD) in the aortic valve position and/or by the support system itself. The method is based in particular on (thermally) anemometric (measuring) principles for flow measurement. The basic principle in this case is that a flowing medium cools a hot body as a function of the flow speed. The method advantageously allows the heart-time volume to also be made available outside of the surgical scenario with comparable quality as when using a dilution catheter. This is particularly advantageous since the heart-time volume ($Q_{HTV}$) has a greater clinical relevance than the pump volume flow ($Q_p$), which is mostly used and only quantifies the flow through the support system itself.

A particular advantage of the method is that, unlike as usual in anemometric methods, no separate heating element is required to generate the heat flow to be measured. Rather, the thermal dissipation loss, which in any case occurs on the electric motor of the LVAD, can be used for anemometric flow measurement. Preferably, no (separate) heating element (except the electric motor) is used to determine the total fluid volume flow. In other words, the electric motor is the only heating element that is used in the solution proposed here. In particular, in the solution proposed here, the thermal dissipation loss occurring on and/or in the electric motor of the support system is used for the (thermally) anemometric or calorimetric flow measurement. It is furthermore preferred that the support system has no (separate) heating element (except the electric motor).

A reference temperature of the fluid is determined, in particular measured, in step a). The reference temperature is preferably determined by a reference temperature sensor, which is particularly preferably a component of the support system. The reference temperature sensor can, for example, be arranged in and/or on an (inlet) cannula of the support system. The reference temperature usually represents a background temperature of the fluid, in other words a fluid temperature which is in particular not influenced by the thermal dissipation loss of the electric motor.

In step b), a motor temperature of an electric motor of the support system is determined, in particular measured. The electric motor can be a component of a flow machine or of a pump of the support system. The support system is preferably arranged on or in the fluid flow such that a heat flow from the support system, in particular from its electric motor, can be dissipated to the fluid flow. The term "motor temperature" can also be understood to mean an internal temperature or (external) surface temperature of the support system, in particular in the region of the electric motor, which in particular allows a preferably direct conclusion about the temperature of the electric motor, in particular about the temperature of a coil package of the electric motor.

The support system is preferably implanted such that it is located in the fluid flow at least partially, preferably completely, or with at least 50%, particularly preferably at least 85%, or even at least 95% of its (external) surface. Furthermore, the support system is preferably located along at least 50%, particularly preferably at least 85%, or even at least 95% of its length in the fluid flow. One end of the support system in the region of which or on which the electric motor is located is preferably at least partially located in the aorta. Furthermore, the opposite end of the support system in the region of which or on which a(n) (inlet) cannula of the support system is located is preferably located at least partially in a ventricle (the left ventricle) of the heart. Furthermore, the support system is preferably arranged in a blood vessel, such as an artery, in particular the aorta, at least partially, preferably completely, or with at least 50%, particularly preferably at least 85%, or even at least 95% of its (external) surface. The support system is particularly preferably implanted such that it is (completely) located in the (descending) aorta.

In step c), the thermal dissipation loss of the electric motor is determined. The thermal dissipation loss of the electric motor is preferably determined by a current sensor, which preferably measures an electrical current of the electric motor.

In step d), the total fluid volume flow is determined using the reference temperature, the motor temperature, and the thermal dissipation loss of the electric motor. In step d), with the aid of at least one heat transfer specification, at least one heat transfer coefficient, at least one calibration factor, and/or at least one blood vessel cross section, in particular an aortic cross section, the total fluid volume flow is determined as a function of the reference temperature, the motor temperature, and the thermal dissipation loss of the electric motor.

According to an advantageous embodiment, it is proposed that the reference temperature is measured in particular spatially and/or temporally before heating the fluid by the electric motor. A reference temperature sensor is preferably arranged at a distance from the electric motor, in particular upstream of the electric motor, preferably on a(n) (inlet) cannula of the support system. The reference temperature sensor is particularly preferably arranged in the region of and/or on an end of the (inlet) cannula opposite the electric motor.

According to an advantageous embodiment, it is proposed that the motor temperature of the electric motor is measured on a surface along which the fluid flows. The surface is generally an (external) surface of the support system that is in contact with the fluid. The motor temperature can, for example, be measured with a motor temperature sensor which is arranged on an (external) surface of the support system in the region of the (internal) electric motor. Alternatively, the motor temperature of the electric motor can be measured inside the motor. For this purpose, a motor temperature sensor can be arranged inside the electric motor.

According to an advantageous embodiment, it is proposed that a flow speed of the fluid is determined, in particular calculated, in step d) as a function of calibration data, the reference temperature, the motor temperature, and the thermal dissipation loss of the electric motor. The calibration data preferably comprise a characteristic length (e.g., tube diameter, possibly approximated in the region of the aortic valve), a kinematic viscosity of the fluid, a temperature conductivity of the fluid, a thermal conductivity of the fluid, and/or a (top) surface of the support system wetted with fluid.

According to an advantageous embodiment, it is proposed that an ascertained cross-sectional geometry of an aorta in the region of the implanted vascular support system is furthermore taken into account in step d). A (flow) cross section of the aorta in the region of the support system is preferably taken into account. This value can be ascertained by a doctor by means of ultrasound or computer tomography, for example. The total fluid volume flow or the heart-time volume can be particularly advantageously determined, in particular calculated, as a function of the flow speed of the fluid, the (flow) cross section of the aorta and a (speed-dependent) calibration factor. The (speed-dependent) calibration factor can, for example, be ascertained by means of a calibration in the context of implantation, e.g., by using a dilution catheter as the reference standard.

According to an advantageous embodiment, it is proposed that a fluid volume flow which flows through the support system is furthermore determined. In other words, this relates in particular to a fluid volume flow that only flows through the support system itself. This fluid volume flow is usually the so-called pump volume flow ($Q_p$), which only quantifies the flow through the support system itself. If this value is known in addition to the total volume flow or heart-time volume ($Q_{HTV}$), the so-called level of support can be calculated from the ratio of $Q_p$ to $Q_{HTV}$ (i.e., $Q_p/Q_{HTV}$). In order to determine the pump volume flow, an established method for measuring the pump volume flow discussed in the beginning in connection with the prior art can be used.

The total fluid volume flow ascertained in step d) is preferably provided as a control parameter for the support system in a step e), for example. A processing unit of the support system can provide this control parameter as an output variable, in particular to a control unit of the support system that preferably regulates the power of the electric motor and thus in particular also the (blood) delivery rate of the support system.

According to a further aspect, a processing unit is proposed, configured to carry out a method proposed here and comprising a memory in which calibration data are stored. As an alternative or in addition to the calibration data, at least one (speed-dependent) calibration factor and/or a thermal model of the electric motor can also be stored in the memory. In addition, the processing unit can comprise a microprocessor which can access the memory. The processing unit preferably receives data from a reference temperature sensor, a motor temperature sensor, and/or a current sensor.

According to a further aspect, an implantable, vascular support system is proposed, comprising:
- a reference temperature sensor for determining a reference temperature of a fluid,
- an electric motor,
- a motor temperature sensor for determining a motor temperature of the electric motor,
- a current sensor for determining at least the current flow through the electric motor or the thermal dissipation loss of the electric motor.

The support system is preferably a left ventricular heart support system (LVAD) or a percutaneous, minimally invasive left-heart support system. Furthermore, the support system is preferably fully implantable. In other words, this means in particular that the means required for the detection, in particular the reference temperature sensor, the motor temperature sensor, and the current sensor, are completely located in the body of the patient and remain there. The support system is particularly preferably configured and/or suitable for being arranged at least partially in a ventricle, preferably in the left ventricle, of a heart and/or in an aorta, in particular in the aortic valve position.

The current sensor is used to determine the current flow through the electric motor and/or the thermal dissipation loss of the electric motor. The current sensor preferably measures the current flow through the electric motor and calculates the dissipation loss of the electric motor therefrom. If the current sensor only supplies the current flow as an output variable, it is in particular provided that the current flow is converted into the dissipation loss of the electric motor in a processing unit of the support system.

The support system furthermore preferably comprises a cannula, in particular an inlet cannula, and a flow machine, such as a pump. The electric motor is regularly a component of the flow machine. The electric motor then drives the flow machine for conveying the fluid. The (inlet) cannula is preferably configured such that in the implanted state, it can guide fluid from a (left) ventricle of a heart to the flow machine. The fluid can be guided through the cannula to the flow machine. The cannula is preferably designed to guide fluid in the form of blood from a (left) ventricle of a heart into an aorta.

The support system is preferably elongated and/or tubular. The inlet cannula and the flow machine are preferably arranged in the region of opposite ends of the support system.

The reference temperature sensor can be arranged on the cannula or near a region of the cannula at a distance from the flow machine. In particular, the reference temperature sensor can be arranged on the cannula or near a region of the cannula facing away from the electric motor. The reference temperature sensor is particularly preferably arranged at a distal end of the cannula, i.e., where the blood flows from a ventricle into the cannula.

The support system can have a tubular elongated structure with a cannula section in which the cannula is formed and with a motor housing section which is connected to the cannula section and in which the electric motor is arranged in a motor housing.

It is advantageous if the reference temperature sensor is arranged in a region of the cannula section at a distance from the motor housing section. The electric motor is preferably arranged in a motor housing around which blood can flow in the aorta.

The support system can furthermore comprise a processing unit configured to determine a total fluid volume flow in the region of the support system using the reference temperature, the motor temperature, and the thermal dissipation loss of the electric motor. The support system is preferably configured to carry out a method proposed here.

The details, features, and advantageous embodiments discussed in connection with the method can also arise accordingly in the processing unit and/or the support system presented here and vice versa. In this respect, reference is made in full to the explanations there regarding the detailed characterization of the features.

BRIEF DESCRIPTION OF THE DRAWINGS

The solution presented here as well as its technical environment are explained in more detail below with reference to the figures. It should be pointed out that the invention is not to be limited by the exemplary embodiments shown. In particular, unless explicitly stated otherwise, it is also possible to extract partial aspects of the facts explained in the figures and to combine them with other components and/or insights from other figures and/or the present description.

The following are shown schematically.

DETAILED DESCRIPTION

Figure 1A:
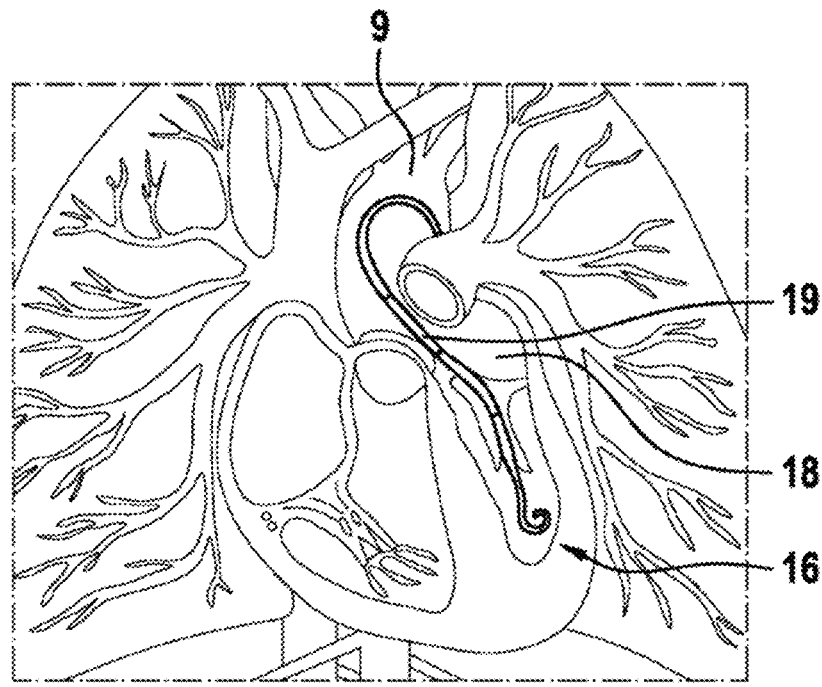
FIG. 1a a percutaneous, minimally invasive left-heart support system.
Figure 1B:
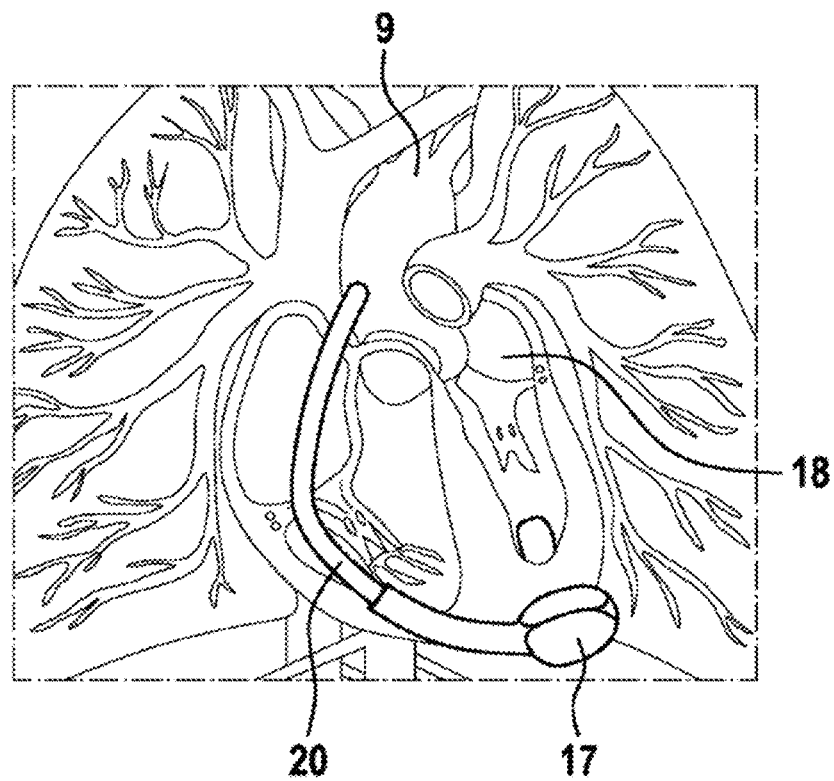
FIG. 1b a left-heart support system invasively implanted under the chest opening, FIG. 2 an implanted vascular support system, FIG. 3 an arrangement of an implanted vascular support system, FIG. 4 a component architecture of a support system, FIG. 5 an illustration of a heat flow, FIG. 6 an illustration of a temperature curve, and FIG. 7 a further illustration of a temperature curve.

Implanted left-heart support systems (LVAD) exist mainly in two design variants, as shown in FIGS. 1a and 1b. FIG. 1a shows a (percutaneous) minimally invasive left-heart support system 16, while FIG. 1b shows a left-heart support system 17 invasively implanted under the chest opening. The variant according to FIG. 1a conveys blood directly from the left ventricle 18 into the aorta 9 since the (percutaneous) minimally invasive left-heart support system 16 is positioned centrally in the aortic valve 19. The variant according to FIG. 1b conveys the blood from the left ventricle 18 via a bypass tube 20 into the aorta 9.

Depending on the level of support, which describes the proportion of volume flow conveyed by a conveying means, such as a pump of the support system, to the total volume flow of blood from the ventricle 18 to the aorta 9, a certain volume flow reaches the aorta 9 via the physiological path through the aortic valve 19. The heart-time volume or the total volume flow ($Q_{HTV}$) from the ventricle 18 to the aorta 9 is therefore usually the sum of the pump volume flow ($Q_p$) and the aortic valve volume flow ($Q_a$).

Figure 2:
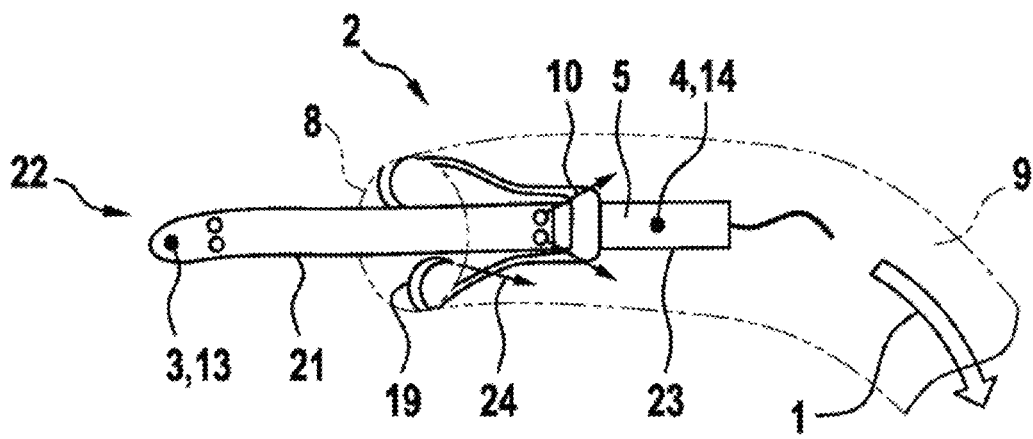

FIG. 2 schematically shows an implantable vascular support system 2 in the aortic valve position. For further illustration, reference is also made simultaneously to the schematic arrangement of the support system 2 according to FIG. 3, wherein the reference signs are used uniformly in all figures.

The support system 2 is here, by way of example, a left ventricular heart support system (LVAD).

The support system has a tubular elongated structure with a cannula section in which an inlet cannula 21 is formed as cannula, and comprises a motor housing section which is connected to the cannula section and in which an electric motor 5 is located in a motor housing 23.

The support system 2 protrudes from the aorta 9 through the aortic valves 19 distally into the ventricle 18. Here, the support system 2 has, by way of example, an inlet cannula 21 which protrudes into the ventricle 18. A fluid volume flow 10 is conveyed, e.g., pumped, through the inlet cannula 21 from the ventricle 18 into the aorta 9 using an electric motor 5 of the support system 2, which drives a flow machine in the form of a pump in the support system 2. Therefore, the fluid volume flow 10 is also referred to as the pump volume flow ($Q_p$), which only quantifies the flow through the support system 2 itself.

Figure 3:
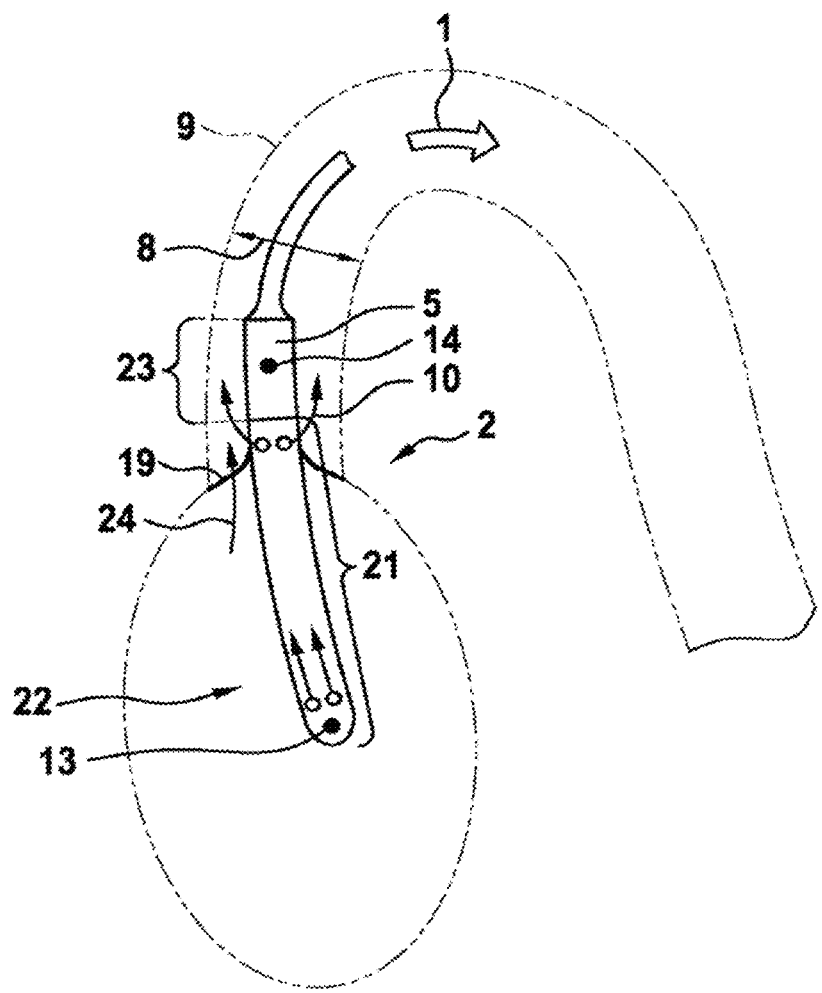

In addition, it can be seen in FIG. 2 and FIG. 3 that a certain aortic valve volume flow 24 reaches the aorta 9 via the physiological path through the aortic valve 19. The heart-time volume or the total fluid volume flow 1 ($Q_{HTV}$), passing through a cross-sectional geometry 8 of the aorta 9 in the region of the support system 2, from the ventricle 18 to the aorta 9 is therefore the sum of the fluid volume flow 10 ($Q_p$) and the aortic valve volume flow 24 ($Q_a$). This is described by the following equation (1).

$$Q_{HTV}=Q_p+Q_a \tag{1}$$

The support system 2 comprises a reference temperature sensor 13 for determining a reference temperature 3 of a fluid, in this case blood by way of example. The support system 2 furthermore comprises an electric motor 5 and a motor temperature sensor 14 for determining a motor temperature 4 of the electric motor 5. In addition, the support system 2 has a current sensor (not shown here) for determining the thermal dissipation loss (not shown here) of the electric motor 5.

The motor temperature sensor 14 is, by way of example, integrated in a motor housing 23, in which the thermal dissipation loss of the electric motor 5 is dissipated to the surrounding fluid. The motor temperature sensor 14 is configured and arranged such that it can measure the motor temperature 4. For this purpose, the motor temperature sensor 14 can be configured and arranged such that it measures a surface temperature of the motor housing 23 or a temperature of the stator (not shown here) of the electric motor 5. In this case, the temperature of the stator can be approximated by an internal temperature in the motor housing 23 between the motor housing 23 and the coil package (not shown here). Alternatively, the temperature in the coil package can also be measured directly.

The reference temperature sensor 13 detects the reference temperature 3, which here is the background blood temperature by way of example. For this purpose, the reference temperature sensor 13 is positioned in the thermally uninfluenced blood flow upstream of the electric motor 5 representing the heat source; here, by way of example, in the region upstream of the electric motor 5. For this purpose, the reference temperature sensor 13, as shown in FIG. 2, is arranged in a region of the cannula section at a distance from the motor housing section at a distal end of the inlet cannula 21, i.e., where the blood flows from a ventricle into the inlet cannula 21.

Figure 4:
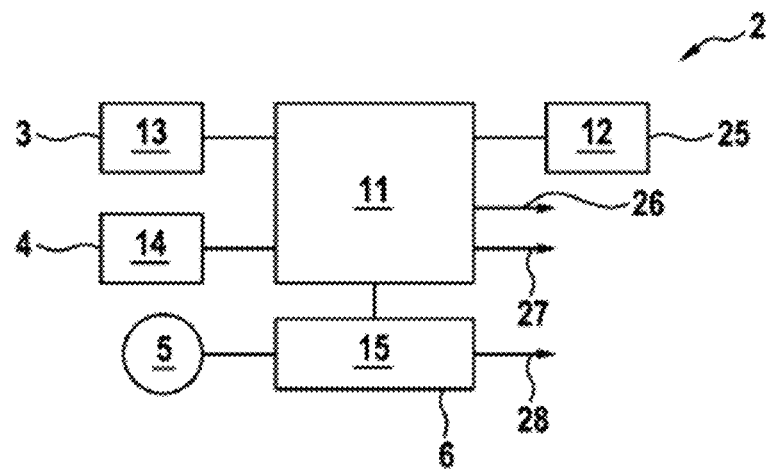

FIG. 4 schematically shows a component architecture of a support system 2. The support system 2 comprises a reference temperature sensor 13 for determining a reference temperature 3 of a fluid, in this case blood by way of example. The support system 2 furthermore comprises an electric motor 5 and a motor temperature sensor 14 for determining a motor temperature 4 of the electric motor 5. In addition, the support system 2 has a current sensor 15 for determining the thermal dissipation loss 6 of the electric motor 5. For this purpose, the current sensor 15 ascertains, by way of example, the current flow (not shown here) through the motor 5 and converts it into the thermal dissipation loss 6. According to the illustration according to FIG. 4, the support system 2 furthermore comprises a processing unit 11 configured to determine a total fluid volume flow (not shown here) in the region of the support system 2 using the reference temperature 3, the motor temperature 4, and the thermal dissipation loss 6 of the electric motor 5. In addition, the support system 2 has an electronically readable memory 12 with calibration data 25.

The measurement data of the reference temperature sensor 13, the motor temperature sensor 14, and the current sensor 15 are transmitted to the processing unit 11. The processing unit 11 processes the measurement data with calibration data 25 from the memory 12 to form the blood flow speed or the (total) blood volume flow. The processing unit 11 furthermore comprises an output 26 to a communication unit (not shown here), an output 27 to a power supply (not shown here), and an output 28 to a motor control (not shown here).

Figure 5:
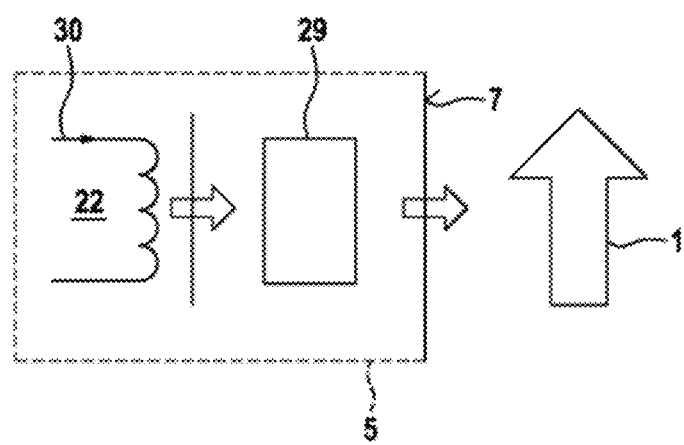

FIG. 5 schematically shows an illustration of an exemplary heat flow (horizontal arrows) through the electric motor 5 to the fluid flow (vertical arrow) or the total fluid volume flow 1. The electric motor 5 in this case comprises, by way of example, a movably mounted rotor (not shown here) and a stationary coil package 22 which is offset by an air gap outside and which is connected to the stator 29. FIG. 5 thus schematically illustrates in other words the thermal conduction transitions from the coil package 22 of the electric motor 5 via the stator 29 to the blood flow. The loss mechanisms in the electric motor 5 primarily relate to the Joule current heat losses Pv (see equation (2) below).

$$P_V = R_{TW} \cdot I^2 \tag{2}$$

Here, $R_{TW}$ denotes the winding resistance of the coil package 22 at the operating temperature $T_W$. The winding resistance $R_{TW}$ in the case of copper is a linear function of the winding temperature $T_W$. This is described by equation (3) below:

$$R_{TW} = R_{25} \cdot (1 + \alpha_{Cu}(T_W - 25)) \tag{3}$$

with the winding resistance $R_{25}$ at 25° C., the winding operating temperature $T_w$, and the constant $\alpha_{cu} = 0.0039 K^{-1}$.

In addition, iron losses also occur, e.g., magnetization losses according to the following equation (4):

$$P_{V,magn} = \pi/30 \cdot M_{Magn} \cdot n \tag{4}$$

and eddy current losses in the back iron material of the stator according to the following equation (5):

$$P_{V,Eddy} = \text{const} \cdot n^2 \tag{5}$$

with the number of revolutions n of the motor and the magnetic friction torque $M_{Magn}$. In addition, bearing losses from the bearing of the motor occur, which are generally negligible.

The thermal resistance between a heat source and a heat sink is measured in Kelvin per watt (K/W). The determining thermal conduction mechanism between the coil package and the blood flow is thermal conduction through the layers of the motor to the outside, as shown in FIG. 5. In order to determine the temperatures, the heat capacities of the individual components traversed by the heat flow as well as the respective heat transfer resistances are required. Since it can be adequately assumed that the electric motor is in stationary operation and thus in thermal equilibrium, the heat capacities are negligible. All necessary parameters can be determined in advance and can be stored in a processing unit.

Figure 6:
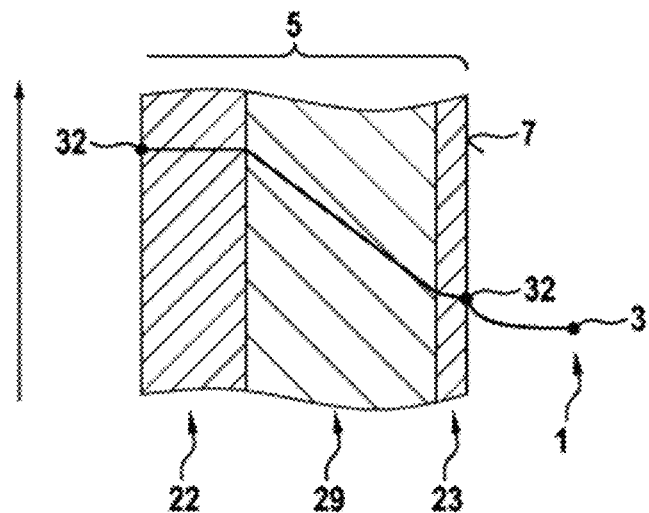

FIG. 6 schematically shows an illustration of a temperature curve along the material layer sequence from the coil package 22 via the stator 29 and the motor housing 23 to the total fluid volume flow 1. FIG. 6 shows a temperature distribution resulting in the thermal equilibrium for a heat flow according to FIG. 5. The highest temperature is present in the heat source, the coil package 22 through which the electrical current flows. The winding temperature 31 (formula symbol $T_W$) of the coil package 22 is therefore the highest temperature in FIG. 6. For simplification, a constant heat distribution over the entire thickness of the coil package 22 was assumed here. Due to the finite thermal conductivity of the stator material and housing material, a linear temperature gradient results via the stator 29 and the motor housing 23, or a logarithmic temperature gradient in the non-simplified case of a cylindrical motor housing 23.

When considering the simplified principle, the winding temperature 31 arising in the coil package 23 (formula symbol $T_W$) is:

$$T_W = T_A + (R_{th1} + R_{th2}) \cdot P_v \tag{6}$$

$$T_W = T_A + (R_{th1} + R_{th2}) \cdot R_{TW} \cdot I^2 \tag{7}$$

$$T_W = T_A + (R_{th1} + R_{th2}) \cdot R_{25} \cdot (1 + \alpha_{Cu}(T_W - 25°C.)) \tag{8}$$

$$T_W = T_A + \frac{(R_{th1} + R_{th2}) \cdot R_{25} \cdot I^2}{1 - \alpha_{Cu} \cdot (R_{th1} + R_{th2}) \cdot R_{25} \cdot I^2} \tag{9}$$

Here, the electrical current flow 30 (formula symbol I) and the surface temperature 32 (formula symbol $T_A$) are the only variable parameters. $R_{th1}$ describes the thermal resistance between the coil package 22 and the stator 29. $R_{th2}$ describes the thermal resistance between the stator 29 and the fluid flow. The current flow 30 (formula symbol I) can be ascertained by measuring with the current sensor 15, for example, in a control device of the current sensor, and is thus precisely known. The surface temperature 32 (formula symbol $T_A$) denotes the temperature on a surface 7 of the electric motor 5 along which the fluid flows. In other words, the surface 7 is in the blood stream.

Figure 7:
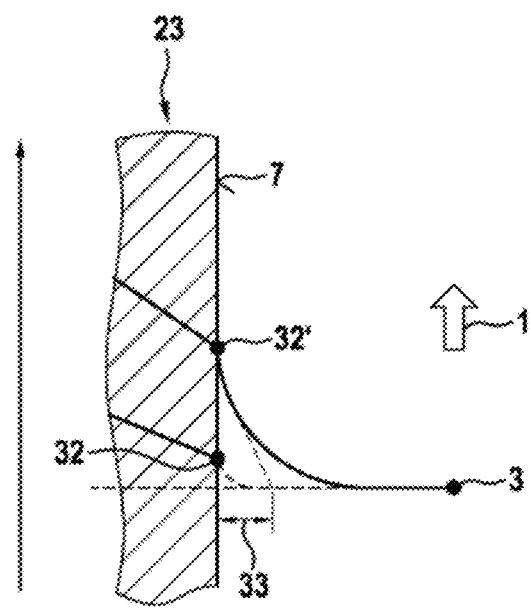

FIG. 7 schematically shows a further illustration of a temperature curve. FIG. 7 shows a detailed view of the illustration according to FIG. 6 in the region of the surface 7 at two different flow speeds. In other words, FIG. 7 illustrates in printed form the dependence of the temperature(s) (surface temperature and thus also stator temperature and thus also coil package temperature) on the flow speed of the fluid flow or of the blood.

As shown in FIG. 7, a liquid film of thickness 33 is formed near the surface 7. The thickness 33 of the liquid film and the temperature difference $T_A$–TB between the surface temperature 32 (formula symbol $T_A$) and the reference temperature 3 (formula symbol $T_B$), which represents the background temperature of the fluid (blood), is a function of the flow speed of the fluid, as illustrated in FIG. 7. According to the illustration in FIG. 7, a lower flow speed of the fluid along the surface 7 leads to a higher surface temperature 32' than the surface temperature 32, which arises at a comparatively higher flow speed.

The heat flow through the liquid film is $$\dot{Q} = \alpha_B(T_B - T_A)A \tag{10}$$

with the heat transfer coefficient $\alpha_B$ from the top of the housing to the blood and the wetted surface A of surface 7. The heat transfer coefficient is defined as $$\alpha_B = \frac{Nu\lambda}{L} \tag{11}$$

with the dimensionless Nusselt number Nu, the thermal conductivity $\lambda$ of the fluid (here: blood), and a reference length L, which can be a tube diameter, for example. It furthermore applies to the Nusselt number averaged across the body surface that it is a function of the dimensionless Reynolds number Re and Prandtl number Pr:

$$Nu = f(Re, Pr) \tag{12}$$

These can each be calculated as a function of the geometry and the flow (Re and Pr) or as a function of the fluid properties (Pr) and stored in the calibration data memory. The Reynolds number is defined as $$Re = \frac{uL}{v} \tag{13}$$

with the characteristic length L (e.g., tube diameter), the kinematic viscosity of the fluid v, and the sought flow speed u. The Prandtl number is a pure substance variable and given by $$Pr = \frac{v}{\alpha} \tag{14}$$

with the temperature conductivity a of the fluid. If the definitions are inserted into the convective heat flow through the liquid film (equation (10)), the relationship between the known heat flow $\dot{Q}$ and the sought flow speed u is obtained. The result of this insertion is shown in equation (15) below. The heat flow $\dot{Q}$ is known from an energy balance. It follows from the energy balance for the stationary case considered here that the heat flow $\dot{Q}$ (in terms of magnitude) substantially corresponds to the thermal dissipation loss 6 (formula symbol $P_V$).

The surface temperature 32 (formula symbol $T_A$) can be measured here, for example, directly on the surface 7 by means of the motor temperature sensor 14, or the motor temperature sensor 14 can measure a temperature inside the motor and the surface temperature 32 (formula symbol $T_A$) is ascertained from the logarithmic temperature relationship to the temperature distribution in the motor housing (cf. FIGS. 6 and 7). The reference temperature 3 (formula symbol $T_B$) is determined by the reference temperature sensor 13. The parameters L, v, a, $\lambda$, and A are generally stored in the system as calibration data.

$$Q = \frac{f\left(\frac{uL}{v}, \frac{v}{\alpha}\right)\lambda}{L}(T_A - T_B)A \tag{15}$$

With known cross-sectional geometry 8 of the aorta 9 of the patient in the region of the support system (ascertainable, for example, by ultrasound, computer tomography, or magnetic resonance tomography), the total fluid volume flow 1 (formula symbol $Q_{HTV}$) can be determined from the flow speed u determined in this way. The corresponding relationship is specified in the following equation (16):

$$Q_{HZV} = k(u)uO \qquad (16)$$

Here, k(u) is a calibration factor dependent on the flow profile, u is the calculated flow speed, and O is the measured aortic cross section (cf. cross-sectional geometry 8).

The solution proposed here allows in particular one of the following advantages:
- Fully implanted, in particular pump-integrated and/or automatic determination of $Q_{HTV}$ instead of only $Q_p$.
- Anemometric measuring methods using the waste heat of a VAD motor instead of an additional heating element do not result in an additional heat input into the organism.
- This also prevents additional current consumption, whereby the battery runtime of autonomous systems is extended.

The invention claimed is:

1. A method for determining a total fluid volume flow of blood in a region of a cardiac support system, comprising: determining a reference temperature of the blood via a reference temperature sensor of the cardiac support system, wherein the cardiac support system comprises: a flow machine configured to convey blood, a cannula configured to guide the blood to the flow machine, wherein the cannula is configured to guide the blood from a ventricle of a heart into an aorta, the reference temperature sensor configured to determine the reference temperature of the blood, an electric motor configured to guide the flow machine, a motor temperature sensor configured to determine a motor temperature of the electric motor, and a current sensor configured to determine at least a current flow through the electric motor or a thermal dissipation loss of the electric motor, determining the motor temperature of the electric motor of the cardiac support system via the motor temperature sensor of the cardiac support system, determining the thermal dissipation loss of the electric motor via the current sensor of the cardiac support system, and determining the total fluid volume flow based on the reference temperature, the motor temperature, and the thermal dissipation loss of the electric motor.

2. The method according to claim 1, wherein determining the total fluid volume flow is based in part on a cross-sectional geometry of the aorta in the region of the cardiac support system.

3. A computer readable storage medium storing therein computer-readable instructions that, when executed by a processing unit, cause the processing unit to: determine a reference temperature of blood flowing in a region of a cardiac support system via a reference temperature sensor of the cardiac support system, wherein the cardiac support system comprises: a flow machine configured to convey blood, a cannula configured to guide the blood to the flow machine, wherein the cannula is configured to guide the blood from a ventricle of a heart into an aorta, the reference temperature sensor configured to determine the reference temperature of the blood, an electric motor configured to guide the flow machine, a motor temperature sensor configured to determine a motor temperature of the electric motor, and a current sensor configured to determine at least a current flow through the electric motor or a thermal dissipation loss of the electric motor determine the motor temperature of the electric motor of the cardiac support system via the motor temperature sensor of the cardiac support system, determine the thermal dissipation loss of the electric motor via the current sensor of the cardiac support system, and determine a total fluid volume flow of the blood based on the reference temperature, the motor temperature, and the thermal dissipation loss of the electric motor.

4. A cardiac support system comprising: a flow machine configured to convey blood a cannula configured to guide the blood to the flow machine, wherein the cannula is configured to guide the blood from a ventricle of a heart into an aorta, a reference temperature sensor configured to determine a reference temperature of the blood, an electric motor configured to guide the flow machine, a motor temperature sensor configured to determine a motor temperature of the electric motor, and a current sensor configured to determine at least a current flow through the electric motor or a thermal dissipation loss of the electric motor.

5. The support system according to claim 4, further comprising a processing unit configured to determine a total fluid volume flow of the blood in a region of the cardiac support system using the reference temperature, the motor temperature, and the thermal dissipation loss of the electric motor.

6. The support system according to claim 4, wherein the reference temperature sensor is arranged on the cannula or near a region thereof at a distance from the flow machine.

7. The support system according to claim 4, wherein the reference temperature sensor is arranged on the cannula or near a region thereof facing away from the electric motor.

8. The support system according to claim 4, further comprising: a tubular elongated structure comprising a cannula section, the cannula section comprising the cannula, and a motor housing comprising a motor housing section configured to connect to the cannula section, wherein the electric motor is arranged in the motor housing.

9. The support system according to claim 8, wherein the reference temperature sensor is arranged in a region of the cannula section at a distance from the motor housing section.

10. The support system according to claim 4, wherein the electric motor is arranged in a motor housing, wherein the motor housing is configured to allow the blood to flow around the motor housing in the aorta.

11. The support system according to claim 8, wherein the motor housing is configured to allow the blood to flow around the motor housing in the aorta.

12. The support system according to claim 8, wherein the motor temperature sensor is configured to measure a surface temperature of the motor housing.

13. The support system according to claim 4, wherein the motor temperature sensor is configured to measure a temperature of a stator of the electric motor.

14. A cardiac support system comprising: a flow machine configured to convey blood, a cannula configured to guide the blood to the flow machine, a reference temperature sensor configured to determine a reference temperature of the blood, an electric motor configured to guide the flow machine, a tubular elongated structure comprising a cannula section, the cannula section comprising the cannula, a motor housing comprising a motor housing section configured to connect to the cannula section, wherein the electric motor is arranged in the motor housing, wherein the motor housing is configured to allow the blood to flow around the motor housing in an aorta, a motor temperature sensor configured to determine a motor temperature of the electric motor, and a current sensor configured to determine at least a current flow through the electric motor or a thermal dissipation loss of the electric motor.

15. The support system according to claim 14, further comprising a processing unit configured to determine a total fluid volume flow of the blood in a region of the cardiac support system using the reference temperature, the motor temperature, and the thermal dissipation loss of the electric motor.

16. The support system according to claim 14, wherein the reference temperature sensor is arranged on the cannula or near a region thereof at a distance from the flow machine.

17. The support system according to claim 14, wherein the reference temperature sensor is arranged on the cannula or near a region thereof facing away from the electric motor.

18. The support system according to claim 14, wherein the reference temperature sensor is arranged in a region of the cannula section at a distance from the motor housing section.

19. The support system according to claim 14, wherein the motor temperature sensor is configured to measure a surface temperature of the motor housing.

20. The support system according to claim 14, wherein the motor temperature sensor is configured to measure a temperature of a stator of the electric motor.

21. The support system according to Claim 19, wherein the reference temperature sensor is arranged on the cannula or near a region thereof at a distance from the flow machine.

22. The support system according to Claim 19, wherein the reference temperature sensor is arranged on the cannula or near a region thereof facing away from the electric motor.

23. The support system according to Claim 19, wherein the reference temperature sensor is arranged in a region of the cannula section at a distance from the motor housing section.

24. The support system according to Claim 19, wherein the motor temperature sensor is configured to measure a surface temperature of the motor housing.

25. The support system according to Claim 19, wherein the motor temperature sensor is configured to measure atemperature of astator of the electric motor.

* * * * *

UNITED STATES PATENT AND TRADEMARK OFFICE
CERTIFICATE OF CORRECTION

PATENT NO. : 12,324,906 B2
APPLICATION NO. : 15/734010
DATED : June 10, 2025
INVENTOR(S) : Hardy Baumbach Page 1 of 1

It is certified that error appears in the above-identified patent and that said Letters Patent is hereby corrected as shown below:

On the Title Page

Page 4, Column 2, item [56], Line 66, delete "Decréet al." and insert -- Decré et al. --.

In the Specification

Column 9, Line 63, delete "$T_A$-TB between" and insert -- $T_A$-$T_B$ between --.

In the Claims

Column 11, Claim 3, Line 67, delete "electric motor determine" and insert -- electric motor, determine --.

Column 14, Claim 25, Line 20, delete "atemperature of astator of" and insert -- a temperature of a stator of --

Signed and Sealed this
Nineteenth Day of August, 2025

Coke Morgan Stewart
*Acting Director of the United States Patent and Trademark Office*